(12) United States Patent
Normant et al.

(10) Patent No.: US 6,723,525 B2
(45) Date of Patent: Apr. 20, 2004

(54) METHODS AND COMPOSITIONS FOR SCREENING MODULATORS OF LIPID KINASES

(75) Inventors: Emmanuel Normant, Antony (FR); Alirio Melendez, Fresnes (FR); Olivier Casamitjana, Paris (FR); François Moreau, Issy les Moulineaux (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/964,860

(22) Filed: Sep. 28, 2001

(65) Prior Publication Data

US 2002/0042091 A1 Apr. 11, 2002

(30) Foreign Application Priority Data

Sep. 29, 2000 (EP) .............................. 00402684

(51) Int. Cl.⁷ ................................. C12Q 1/48
(52) U.S. Cl. .................. 435/15; 435/69.2; 435/375
(58) Field of Search ................. 435/15, 69.1, 69.2, 435/193, 194, 375

(56) References Cited

U.S. PATENT DOCUMENTS

| | | | |
|---|---|---|---|
| 4,568,649 A | | 2/1986 | Bertoglio-Matte .......... 436/534 |
| 5,677,189 A | * | 10/1997 | Igarashi et al. ............... 436/57 |
| 6,098,631 A | * | 8/2000 | Holoshitz et al. ........... 128/898 |

FOREIGN PATENT DOCUMENTS

| | | | |
|---|---|---|---|
| EP | 0 154 734 | | 8/1990 |
| EP | 0381514 B1 | * | 5/1995 |
| WO | WO 91/08489 | * | 6/1991 |
| WO | WO 99/12533 | * | 3/1999 |
| WO | WO 99/61581 | | 12/1999 |
| WO | WO 00/00207 | | 1/2000 |
| WO | WO 0037613 | | 6/2000 |

OTHER PUBLICATIONS

Yatomi Y. N,N—Dimethylsphinosine Inhibition of Sphingosine Kinase and Sphingosine 1–Phosphage Activity in Human Platelets. Biochemistry 35, 626–633, 1996.*

Yatomi et al, "N,N–Dimethylsphingosine Inhibition of Sphingosine . . . ", Biochemistry, 1996, 3, 626–633; XP 000647642.

* cited by examiner

*Primary Examiner*—Ralph Gitomer
(74) *Attorney, Agent, or Firm*—Nixon & Vanderhye P.C.

(57) ABSTRACT

The present invention relates to methods of screening compounds that modulate lipid kinases activity. The invention is more preferably based on the SPA technology to screen compounds that modulate the activity of lipid kinases, in particular membrane lipid kinases, more specifically sphingosine kinases. The invention also includes compositions, products, kits, etc for use in performing the above methods, as well as the compounds identified by said methods, and their uses.

26 Claims, 9 Drawing Sheets

First step:
enzymatic reaction

Second step:
phosphorylated sphingosine
binds to the beads

• [$^3$H]sphingosine
(in triton micelle)

•P⁻
Phospho-[$^3$H]sphingosine

• sphingosine

SphK: sphingosine kinase

METHODS AND COMPOSITIONS FOR SCREENING MODULATORS OF LIPID KINASES

FIELD OF INVENTION

The present invention relates to methods of screening compounds that modulate lipid kinases activity. The invention is more preferably based on the SPA technology to screen compounds that modulate the activity of lipid kinases, in particular membrane lipid kinases, cytosolic lipid kinases, secreted lipid kinases and more specifically sphingosine kinases. The invention also includes compositions, products, kits for use in performing the above methods, as well as the compounds identified by said methods, and their uses.

BACKGROUND OF THE INVENTION

Lipid kinases are enzymes that catalyse the phosphorylation of lipids within cells. These enzymes, and the resulting phosphorylated lipids and lipid derived biologically active organic molecules, play a role in many different physiological processes, including cell proliferation, migration, adhesion, differentiation, activity, etc. A particular group of lipid kinases comprises membrane lipid kinases, i.e., kinases that catalyse the phosphorylation of lipids contained in or associated with cell membranes. Examples of such enzymes include phosphinositide(s) kinases (such as PI3-kinases); diacylglycerol kinases; and sphingosine kinases.

Sphingosine kinases (SPHK) convert the substrate sphingosine to sphingosine-1-phosphate (S1P). S1P is involved in various physiological processes, both within cells and upon release in extracellular medium. In particular, reported physiological roles of S1P within cells include the release of calcium from stores, activation of cyclin-dependent kinases, key signalling intermediate in Fc receptor initiated cascades, fMLP induced enzyme release, TNF-α induced (in endothelial cells) adhesion molecule expression, and depression of excitability in ventricular myocytes. Furthermore, when released from the cells, S1P is involved through specific G protein coupled (couple EDG-receptors) for instance in the control of cell proliferation, chemotaxis (attraction and activation of macrophages), cytoskeletal changes (stress fiber formation and cell shape changes, and secretion), cell attachment (fibronectin matrix assembly) and assembly and phosphorylation of paxillin and p125-FAK. Moreover, PDGF induces high levels of sphingosine kinase activity and S1P generation in platelets. In fact, S1P is released from activated platelets in large amounts. This could indicate a potential important role of S1P in inflammation following injury. More particularly, S1P could play an important role in early atherogenesis and fibrosis. Furthermore, sphingosine kinases activity play a major role in regulating calcium signals in mast cells activated via the high affinity IgE receptor (FcεRI), as well as in macrophages triggered by the high affinity IgG receptor (FcγRI), and activation of these cells are very important in allergic and auto-immune diseases, such us but not limited to, asthma and rheumatoid arthritis.

Accordingly, lipids, in particular membrane, cytosolic or secreted lipids, more specifically sphingosine-1-phosphate represent an interesting target for the development of drugs or pharmacologically active compounds. In particular, compounds having the ability to modulate the levels of S1P in cells would represent high potential compounds for the treatment of all diseases wherein S1P is involved such as cardiovascular diseases including atherosclerosis, thrombosis and dyslipidemia, diabetes including type I and type II diabetes and particularly type I diabetes, stroke, autoimmune and inflammatory diseases such as multiple sclerosis, psoriasis, epidermodysplasia verruciformis and inflammatory arthritis, allergic diseases such as dermatitis, T helper-1 related diseases, chronic obstructive pulmonary disease, asthma, cancer and neurodegenerative disorders.

The availability of assays suitable to screen compounds having such property would thus be of major interest. In this respect, the sphingosine kinase (SPHK) activity is classically measured using $^{33}P$ or $^{32}P$ incorporation, followed by lipid extraction and thin layer chromatography (TLC) separation of $^{33}P$ or $^{32}P$ sphingosine-1-P (A. Melendez et al., 2000). However, although this test is very sensitive, it is not suitable for high throughput screening, and no such test or method using TLC has been reported in the art, allowing efficient identification of lipid kinase modulators in high throughput format.

SUMMARY OF THE INVENTION

The present invention discloses compositions and methods for the screening of compounds that modulate, inhibit or activate the activity of lipid kinases, with reliability and efficacy. The methods according to this invention are simple, reliable, sensitive, convenient and economical, and allow screening of compounds, on a high throughput basis. In particular, the invention can be used to screen, in parallel, large numbers of compounds, including combinatorial libraries of compounds, to identify drug candidates or targets. This type of invention thus allows, for the first time, to screen active compounds using lipid kinases as targets, in particular SPHK, for the selection, improvement and/or development of therapeutically active products.

An object of this invention resides more specifically in a method of selecting or identifying a compound that modulates the activity of a lipid kinase, comprising (i) mixing (or contacting) the lipid kinase and a labeled lipid substrate thereof in the presence of a candidate compound and a source of phosphate, (ii) exposing the reaction mixture of (i) to a support material, wherein the support material binds the phosphorylated lipid (that has been phosphorylated by the lipid kinase) and essentially does not bind the unphosphorylated lipid, and (iii) assessing the amount of phosphorylated lipid bound to the support.

The support material may be composed of or comprise various elements, such as polymers, gels, glass, artificial or organic elements, etc . . . and more precisely components selected from yttrium-silicate, yttrium-oxyde or polyvinyltoluene (PVT). The support may further comprise (poly) acrylamide, agarose, sepharose or polystyrene or may be further functionalized, and may be shaped into various forms, including beads.

According to preferred embodiments, the method uses the scintillation proximity technology (SPA). In said embodiments, the support material further comprises a scintillant, which can be excited upon binding of the phosphorylated, (radio)labeled lipid substrate.

In a typical embodiment of the invention the lipid substrate is in a micelle and the source of phosphate is ATP.

The lipid kinase is a cell or membrane extract or may be purified. The lipid kinase may also be is a recombinant enzyme.

In a preferred embodiment, the reaction mixture in (i) comprises:

0.01–10 µM of unlabeled lipid
0.01–10 µCi of radio-labelled lipid,
0.1 to 5% of detergent, such as Triton, or neutral lipid, such as phosphatidyl serine or cardiolipine, or serum proteins from mammalian origin such as BSA (bovine serum albumin), HAS (human serum albumin) or FBSA; or a mixture thereof,
0.1 µM to 1 mM of phosphate source, such as ATP, and the desired amount of total proteins of a cell preparation comprising a lipid kinase (or any composition or material comprising the same) at the appropriate dilution.

In this regard, a more particular aspect of this invention resides in a method of selecting or identifying a compound that modulates, inhibits or activates the activity of a lipid kinase, comprising (i) mixing the said lipid kinase and a labeled lipid substrate thereof in the presence of a candidate compound and a source of phosphate, (ii) exposing the reaction mixture of (i) to beads, wherein the beads bind the lipid in phosphorylated form and essentially do not bind the lipid in unphosphorylated form, the beads further comprising a scintillant which is excitable by the labeled lipid upon binding thereof to the beads, and (iii) assessing the activity of the compound by assessing the scintillation of the beads. The invention can be used for selecting, identifying, characterizing, improving, comparing, etc . . . compounds that modulate, inhibits or activates the activity of lipid kinases. The invention is more particularly suited for screening modulators of membrane lipid kinases, cytosolic lipid kinases or secreted lipid kinases, even more preferably sphingosine kinases.

A further object of this invention resides in a kit for use in the above screening assay, comprising a labelled lipid and/or a support as defined above.

A further object of this invention resides in the use of compounds selected or identified using the above methods, for pharmaceutical, therapeutical or experimental purposes.

LEGEND TO THE DRAWINGS

FIG. 4: Effect of [$^3$H]sphingosine enzyme on Sphingosine Kinase activity profiles (Triton=0.25%) (4A) and ATP concentration on the signal (4B)

FIG. 5: Effect of Triton (5A) and DMSO (5B) on SphK activity

DETAILED DESCRIPTION OF THE INVENTION

As indicated, this invention resides, generally, in improved methods of screening for modulators of lipid kinases. These methods, generally, use labeled lipid substrates, and more preferably unlabelled phosphate source. The methods can be used to screen activators as well as inhibitors of lipid kinases as modulators of these enzymes, i.e., compounds that increase or decrease the levels of phosphorylated substrate specific for lipid kinases. Preferably, inhibitors are selected, i.e., compounds that decrease the levels of phosphorylated substrate specific for a lipid kinase, typically by at least 20%, preferably by at least 50%.

In a typical embodiment, the method comprises (i) mixing the lipid kinase and a labeled lipid substrate thereof in the presence of a candidate compound and a source of phosphate, (ii) exposing the reaction mixture of (i) to a support material, wherein the support material binds the phosphorylated lipid (that has been phosphorylated by the lipid kinase) and essentially does not bind the unphosphorylated lipid, and (iii) assessing the amount of phosphorylated lipid bound to the support.

In a preferred embodiment, the amount of lipid bound to the support in the presence of a candidate compound is compared to the amount of lipid bound to the support in the absence of a candidate compound, compounds modulating said amount representing compounds that modulate the activity of the lipid kinase.

While several assay formats can be used to carry out the method of the present invention, a preferred assay format is scintillation assays such as the scintillation proximity assay (SPA). Scintillation proximity assay (SPA) technology involves the use of scintillant beads that contain an organic scintillant such as PPO. Assays are usually carried out in aqueous buffers using radioisotopes such as $^3$H, $^{125}$I, $^{14}$C, $^{35}$S or $^{33}$P that emit low-energy radiation, the energy of which is easily dissipated in an aqueous environment. For example, the electrons emitted by $^3$H have an average energy of only 6 keV and have a very short path length (~1~tm) in water. If a molecule labelled with one of these isotopes is bound to the bead surface, either directly or via interaction with another molecule previously coupled to the bead, the emitted radiation will activate the scintillant and produce light. The amount of light produced, which is proportional to the amount of labelled molecules bound to the beads, can be measured conveniently with a liquid scintillation (LS) counter. If the labelled molecule is not attached to the bead, its radiation energy is absorbed by the surrounding aqueous solvent before it reaches the bead, and no light is produced. Thus, bound ligands give a scintillation signal, but free ligands give a very low background, and the need for a time-consuming separation step, characteristic of conventional radioligand binding assays, is eliminated. The manipulations required in the assays are reduced to a few simple pipetting steps leading to better precision and reproducibility, and a higher throughput.

In a more preferred embodiment, the method comprises the binding of radio-labelled phosphorylated lipids (e.g., sphingosine-1-P) to SPA beads. The binding is preferably carried out through chemical or physical interaction with yttrium-silicate or yttrium-oxyde beads, although other binding means can be contemplated. More specifically, the binding is due to the interaction (i-e bound other than covalent bound) between the phosphate group of the phosphorylated substrate and the support surface. The assay medium or reaction comprises a (recombinant) lipid kinase (e.g., hSPHK,) and ATP. What is measured is the ability of the candidate compound to prevent or increase the conversion of labelled unphosphorylated lipid (e.g., sphingosine) to labelled phosphorylated lipid (e.g., S1P) by action of the lipid kinase. For instance, if the candidate ligand inhibits hSPHK, hence the conversion of sphingosine will not occur and a signal not substantially different from the background noise signal will be recorded. On the other hand, if no hSPHK inhibition occurs, sphingosine phosphorylation will take place and a signal resulting from the interaction between labelled S1P and the SPA bead will be recorded.

This invention stems from the unexpected discovery that support material can be designed to bind phosphorylated lipids and not unphosphorylated forms thereof. The invention also shows that cell lysates can be used, at room temperature, without altering the efficacy and selectivity of the assay. The invention further shows that high throughput is feasible, since 384-wells plates format can be used, with low volumes, and that the presence of DMSO does not alter the reliability of the assay.

The Support Material

The present invention now discloses a novel method of screening active compounds using particular support material. The support material has the ability to bind the product of the enzymatic activity such as the phosphorylated lipid but not bind the substrate such as the unphosphorylated lipid. Accordingly, the amount of lipid bound to the support is directly correlated to the lipid kinase activity in the reaction medium. The support may comprise either functional groups allowing said discrimination between phosphorylated and unphosphorylated lipids, such as antibodies or other reactant groups, or be composed of (or comprise) a material having the capacity to distinguish said products.

In this regard, the support may be composed, at least in part, of silicate, polyvinyltoluene (PVT), (poly)acrylamide, agarose, sepharose, polystyrene, etc. Specific examples of support material include PVT or silicate material, optionally coated with ligands such as WGA, streptavidin, polylysine, etc. More preferred material comprises yttrium-oxyde or yttrium silicate (YtSi), optionally coated or functionalized, or PVT.

In a more preferred embodiment, the support contains a scintillant (or an organic scintillant). The scintillant is preferably water insoluble and excitable to a higher energy state upon binding of the labeled lipid to the support. The scintillant should produce sufficient light energy to be detected using suitable device (scintillation counter, for instance). A typical example of scintillant is diphenyloxazole (PPO). This scintillant is efficiently excited by radioisotopes emitting beta rays.

Suitable support material for use in the present invention may be found in the commerce, such as for instance from Amersham products WGA-coated PVT beads (RPNQ0001), PEI-treated WGA PVT beads (RPNQ0003), streptavidin-coated PVT beads (RPNQ0007), polylysine-coated yttrium silicate beads (RPNQ0010), WGA coated yttrium silicate beads (RPNQ0011), streptavidin coated yttrium silicate beads(RPNQ0012) and RNA-binding yttrium silicate SPA beads (RPNQ0013) or RNA-binding yttrium oxyde SPA beads (RPNQ0280).

The ability of the support material to discriminate between phosphorylated and unphosphorylated lipids can be determined (or verified) using conventional binding experiments as described in the examples. Typically, the support material can be contacted, separately, with a phosphorylated and unphosphorylated labeled lipid. Binding (or absence of binding) can be verified by assessing the amount of label attached to the support. It should be understood that residual binding of the unphosphorylated lipid may be tolerated, as long as the difference in binding with phosphorylated lipid is sufficiently important.

In a specific example, the support material comprises cerium-doped yttrium ion silicate (y2SiO5:Ce). The support may be composed entirely of the above material, or comprise additional components such as (poly)acrylamide, agarose or polystyrene. A specific example of a support material for use in the instant invention is the RNA-binding yttrium silicate SPA beads (RPNQ0625 or RPNQ0013, Amersham). Another specific example is the Yttrium oxyde SPA beads (RPNQ0280, Amersham).

Generally, from 0.05 to 5 mg of support material is used for each assay. It should be understood that the precise amount of support material can be adjusted by the skilled person, depending on the support material, amounts of reagents, etc. Furthermore, in this step, it is possible to add, to the reaction mixture or buffer, Zn ions to improve the performance of the assay. Preferred quantity of support material is about 0.5 mg by well particularly in 384 well plate. For instance, in a preferred embodiment the support material is yttrium oxide beads.

The Labelled Lipid

As indicated above, this invention employs a labelled lipid, whose phosphorylated form is detected, under the conditions described above. The use of a labelled lipid, as opposed to a labelled source of phosphate (such as ATP) is advantageous since it avoids non-specific signal due to any direct interaction between the source of phosphate and the support material.

The labelled lipid is preferably radiolabelled. Radiolabeling can be performed using various radioisotopes, including $^3H$, $^{125}I$, $^{14}C$, $^{35}S$, $^{33}P$ or $^{32}P$. Preferably, the radioisotope should emit low-energy radiation, the energy of which is easily dissipated in an aqueous environment. Indeed, it is required that unbound labeled substrate essentially fails to activate the scintillant contained in the support material. The nature of the isotope may be selected also depending on the type of scintillant. For instance, where PPO is used as a scintillant, the isotope should preferably emit beta rays, such as $^3H$ for instance.

The amount of labeled lipid used for the assay can be adjusted by the skilled person. In a typical experiment, between 0.01 to 10 $\mu M$ and preferred between 0.02 to 1 $\mu M$ of substrate are used for each assay including 0.01 to 0.5$\mu$ Ci of [$^3H$] sphingosine. The amount of protein to add in the reaction mixture depends on its activity and can be adjusted by the skilled person. Preferably, this amount should lead to less than 30% consumption of the substrate within the reaction time.

Furthermore, in a specific variant, the lipid is incorporated in a micelle. Indeed, the invention shows that efficient screening conditions are obtained when the substrate lipid is present in a micelle. To that effect, it is possible to add a detergent, a neutral lipid or a serum protein (or any mixture thereof) to the reaction mixture, typically within the range of about 0.1 to about 5%, more preferably from about 0.2 to about 3%. More particularly, the detergent may be Triton or Nonidet, the neutral lipid may be phosphatidyl serine or cardiolipine, and the serum proteins are of mammalian origin, such as BSA (bovine serum albumin), HAS (human serum albumin) or FBSA.

In a more preferred embodiment, a detergent is added, such as Triton or Nonidet, within the range of about 0.1 to about 5%, more preferably from about 0.1 to about 3% and most preferred from 0.1 to 1%.

Accordingly, in a specific variant, the reaction mixture in step (i) comprises the radio-labeled and unradio-labeled lipids (such as radio-labeled sphingosine), a source of phosphate, a detergent (such as Triton) or a neutral lipid, and cell extract comprising the lipid kinase (or any composition or material comprising the same). The reaction mixture may comprise any solvent, buffer, saline solution, aqueous solution, etc., that allows contacting of the various reagents and does not alter their biological activity.

In an other specific variant, the reaction mixture in step (i) comprises the radio-labeled lipid (such as a radio-labeled sphingosine), unradio-labeled lipids, a source of phosphate, a detergent (such as Triton) or a neutral lipid, and the lipid kinase (or any composition or material comprising the same). The reaction mixture may comprise any solvent, buffer, saline solution, aqueous solution, etc., that allows contacting of the various reagents and does not alter their biological activity.

More preferably, the reaction mixture in step (i) comprises the radio-labeled lipid (such as a radio-labeled sphingosine), an unradio-labeled lipid, a source of phosphate, a detergent (such as Triton), and cell extracts or preparation containing the lipid kinase.

Furthermore, to facilitate the formation of micelles, the reaction mixture may be further sonicated, although this is not required for performing the assay.

The Lipid Kinase

The lipid kinase may be used under various conditions. Indeed, it is possible to use purified enzyme, or any solution or suspension or composition comprising the enzyme, such as cell fractions, cell lysates, or any cell preparation comprising the active enzyme. This invention indeed shows that it is not required to purify and isolate the enzyme for use in the assay, and that cell lysates provide remarkable results, both in terms of efficacy and specificity. In a preferred embodiment of the instant invention the lipid kinase is used non-purified.

In a particular embodiment, the method uses a preparation comprising the lipid kinase derived (or obtained) from (recombinant) mammalian, bacterial or insect cells, more preferably a cell lysate or cell fractions, or a pre-purified or enriched solution derived therefrom.

The enzyme may be of various origin, such as human or animal, preferably human. The enzyme may be a naturally-occurring enzyme, isolated or prepared from a biological sample that naturally produces the said enzyme (tissue culture, cell culture, etc.), or a recombinant enzyme, prepared from cells containing a recombinant nucleic acid encoding the same.

In this respect, in a particular embodiment, the lipid kinase is obtained from a culture of mammalian cells, preferably human cells, cultured under conditions allowing the synthesis of the enzyme.

Where the enzyme is a sphingosine kinase, it can be prepared from procaryotic cells as well as eucaryotic cells (mammalian, preferably human) cells such as fibroblasts, platelets, monocytes, macrophages, mast cells, T cells etc. Furthermore, the cells may be stimulated to trigger higher enzymatic activity, in particular in the presence of ligands such as, growth factors (e.g. PDGF; EGF; FGF etc . . . ) and via the activation of immune-receptors (e.g. TCR; FcεRI and FcγRI). The cells may be cultured in any appropriate medium, and then treated to prepare the lipid-kinase-containing material (cell extracts, fractions, and the like). Typically, the cells are subjected to physical and/or chemical treatment, to produce the lipid-kinase-containing material. In a typical experiment, the cells are subjected to enzymatic and/or chemical and/or physical lysis, preferably using trypsin, thaw/freeze cycle(s), ultra-sounds, etc., either alone or in various combinations. The cell extracts (or fractions) are collected, and may be further concentrated, suspended in appropriate buffers, purified, conditioned, etc.

Sphingosine kinase may also be obtained from transfected cells containing a nucleic acid encoding said enzyme. In this regard, the nucleic acid sequence encoding a human sphingosine kinase has been described in Melendez et al. *GENE* 251, 19–24. The sequence may be transfected into cells, using various plasmids and/or vectors, containing various promoters, to produce the recombinant enzymes. The lysate of such cells (or other preparations derived therefrom) may be used in the screening assays of this invention.

In a preferred embodiment, the Sphingosine Kinase is obtained from procaryotic cells and preferably from insect cells such as Sf9 or Sf 21. The cells are transfected or infected by a vector comprising the nucleic acid sequence encoding the said enzyme. In this regard, baculovirus is a preferred vector and enzyme production is made according to "Baculovirus Expression Vectors" Davis R. O'REILLY, Lois K. MILLER, Verne A. LUCKOW incorporated herein by reference. However, any assay for protein production by baculovirus known by the skilled artisan is also usable in the contexte of the present invention.

Typically, the kinase preparation used is a cell lysate or fractions (or other material derived from cells) comprising between 0.1 to 40 μg of total proteins, more preferably between 0.1 to 5 μg of total proteins, even more preferably about 1 μg of total proteins. The kinase preparation may also comprise total (transfected) cell extracts. The precise amounts can be adjusted by the skilled person. Generally, the amount of kinase required in the screening of this invention is the amount of kinase which uses during the incubation period of the assay less than one third of the substrat. Preferably, this amount should lead to less than 10% consumption of the substrate within the reaction time.

Alternatively, purified (recombinant) enzymes may be used.

The assay can be performed in any appropriate support or device, including plate, tube, flask, and the like. Generally, contacting is performed in multi-well plates, allowing multiple assays to be carried out in parallel. Typical supports include microtiter plates, especially the 96-well or 384-well and higher throughput microtiter plate formats, which are easy to manage and easy to illuminate with conventional excitation. Other formats may also be used, including larger microtiter plates or nanotechnologies.

Depending on the support and test compound, varying amounts of reagents can be used in the assay. Typically, the following amounts may be distributed in a final maximum volume of 250 µl per well:

0.01 to 10 µM of unlabeled lipid 0.01 to 10 µCi of radio-labelled lipid, 0.1 to 5% of detergent, such as Triton, or neutral lipid, such as phosphatidyl serine or cardiolipine, or serum proteins from mammalian origin such as BSA (bovine serum albumin), HAS (human serum albumin) or FBSA; or a mixture thereof, 0.1 µM to 1 mM of phosphate source, such as ATP, and the desired amount of total proteins of a cell preparation comprising a lipid kinase (or any composition or material comprising the same) at the appropriate dilution.

In a preferred embodiment, the reagents are in the following ranges of quantity in a final volume comprised between 30 µl and 100 µl:

0.01 to 1 µM of unlabeled lipid 0.01 to 0.5 µCi of radio-labelled lipid, 0.1 to 0.5% of detergent, such as Triton, or neutral lipid, such as phosphatidyl serine or cardiolipine, or serum proteins from mammalian origin such as BSA (bovine serum albumin), HAS (human serum albumin) or FBSA; or a mixture thereof, 0.1 µM to 50 µM of phosphate source, such as ATP, the desired amount of total proteins of a cell preparation comprising a lipid kinase (or any composition or material comprising the same) at the appropriate dilution.

In further preferred embodiment 0 to 30% of glycerol is added to the reaction mixture. Preferably 15% to 25% of glycerol is added and most prefered about 20% is added to the reaction mixture.

It should be understood that the precise respective amounts (or concentration) of reagents and test compounds can be adjusted by the user, depending on the type of compound, the type of lipid kinase, the length of incubation period, etc. Furthermore, if necessary, the enzyme can be mixed in the presence of additional agents to improve the performance of the assay.

Furthermore, while ATP is a preferred source of phosphate.

The mixing in step i) can last for up to 6 hours, typically less than 4 hours. Indeed, the various reagents are preferably incubated for a period of time sufficient to allow phosphorylation to occur. Depending on the assays, this period usually lasts less than about 3 hours. In a typical experiment, the mixing is performed for about 1 hour or less and preferably about 45 minutes. In step (ii), the support is added for about 10 minutes to several hours. Depending on the total volume of the reaction mixture, the latter is shaken during the first 5–30 minutes. The mixture is then left for a period of time between 15 minutes to 24 hours. When the support is beads, the beads solution may comprise between 0 to 70% of glycerol and preferably more than 20%. For instance, in 96 wells plate format assay 70% of glycerol is preferably added in beads solution and 20% of glycerol is added in beads solution for the 384 wells plate assay.

The amount or quantity of lipid bound to the support can be assessed by various ways, as an indication of the activity of the lipid kinase. Generally, it is assessed by scintillation counting using conventional devices. Where SPA-derived method is used, the counts are measured directly in the reaction mixture, with no need for any separation step. Alternatively, the support bound lipid may be detected or quantified using other conventional techniques, such as chromatography, immuno-assay,etc.

The test (or candidate) compound(s)

The test compound can be any product in isolated form or in mixture with any other material (e.g., any other product (s)). The compound may be defined in terms of structure and/or composition, or it may be undefined. For instance, the compound may be an isolated and structurally-defined product, an isolated product of unknown structure, a mixture of several known and characterized products or an undefined composition comprising one or several products. Examples of such undefined compositions include for instance tissue samples, biological fluids, cell extracts, vegetal preparations, etc. The test compound may be any organic or inorganic product, including a polypeptide (or a protein or peptide), a nucleic acid, a lipid, a polysaccharide, a chemical product, or any mixture or derivatives thereof. The compounds may be of natural origin, synthetic origin, including libraries of compounds.

As will be further discussed below, the present invention is particularly adapted for the screening of large numbers of compounds, such as combinatorial libraries of compounds. Indeed, the instant invention provides compositions and methods allowing efficient and simple screening of several compounds in short periods of time. In particular, the instant methods can be partially automated, thereby allowing efficient and simultaneous screening of large sets of compounds.

Generally, the activity of the test compound(s) is unknown, and the method of this invention is used to identify compounds exhibiting the selected property (e.g, lipid kinase modulators). However, in particular instances where the activity (or type of activity) of the test compound (s) is known or expected, the method can be used to further characterize said activity (in terms of specificity, efficacy, etc.) and/or to optimise said activity, by assaying derivatives of said test compounds.

A further object of the present invention resides in the use of a compound obtained, identified, selected or characterized as defined above, in the pharmaceutical industry, as a medicament, drug candidate, lead for further optimisation, etc. These compounds may for instance be used for the manufacture of a composition for the treatment of the human body, in particular for the treatment of various pathological conditions such as cardiovascular diseases, diabetes, stroke, autoimmune and inflammatory diseases, allergic diseases such as dermatitis, T helper-1 related diseases, chronic obstructive pulmonary disease, asthma, cancer and neurodegenerative disorders.

The invention also relates to a pharmaceutical composition comprising a compound obtained, identified, selected or characterized as defined above as well as a compound obtainable, identiable, selectable or chracterizable by the method of the instant invention.

The invention also includes kits for use in screening a lipid kinase modulators, the kits comprising a labeled lipid substrate of the lipid kinase and or a support material as defined above. The kit may further include the reagents and/or protocols for SPA technology, such as the lipid kinase itself, buffers, etc.

Further aspects and advantages of the present invention will be disclosed in the following examples, which should be regarded as illustrative and not limiting the scope of the present application.

Material & Methods

Material

Growth medium including all supplements were purchased from LifeTech (Paris, France). Transfection reagents were from QIAGEN (Paris, France). All lipids were purchased from Sigma (Paris, France). [3-3H]sphingosine, 15 mCi/mmole were from Amersham (Paris, France) or NEN (Boston, Ma). Yttrium silicate RNA binding beads and Yttrium oxyde RNA binding beads are from Amersham (Paris, France).

Transfection of Human Sphingosine Kinase (huSPHK1) in CHO or COS-7 Cells

CHO and/or COS-7 cells were cultured in 90% Ham F12 medium, 10% foetal bovine serum, Gentamycin, in T-175 tissue culture flasks in air with 5% $CO_2$ atmosphere at 37° C. CHO and/or COS-7 cells were transiently transfected with the vector pcDNA3 alone or vector containing the human sphingosine kinase cDNA, using the Qiagen reagent Superfect. They were seeded $5 \times 10^6$ per 175 cm$^2$ flask. After 24 hrs, cells were transfected with 10 µg of cDNA mixed with 20 µl Superfect for 6 hrs, washed, and cultured for 2 days in complete Ham medium. They were then trypsinized, centrifuged down at 1500 rpm for 10 min, and resuspended in assay buffer. They underwent 3 thaw/freeze cycles and protein concentration were estimated using the Bradfaord technique (Biorad kit). The protein concentration was adjusted to 1 µg/µl, and aliquots were kept frozen at −20° C.

Sphingosine Kinase Production in BL21DE3 Cells

The culture of BL21DE3/SK cells is inducted with IPTG 50 µM at 25° C. for all the night. The bacterial pellet is suspended in the buffer A. 2 mg/ml of lysosyme is added and the preparation is stirred for 30 min at 4° C. After, addition of Mgcl (10 mM) then DNA' ase 1 (10 µg/ml) is added and the mixture is stirred for 30 min at 4° C. The solution is sonicated around four times for 10 sec at 4° C. The cell sonicate is centrifuged at 4000 rpm for 15 min at 4° C. The supernatant obtained is stored at −20° C.

Assay buffer: Tris Hcl 20 mM, glycerol 20%, β-Mercaptoethanol 1 mM, EDTA 1 mM, Soduim orthovanadate 1 mM, Deoxypyridoxine 0.5 mM, Protease inhibitor coktails complete (Roche, ref 1697498)

Sphingosine Kinase Production in Insect Cells

Sf9 cells are infected by baculovirus according to the method previously mentioned. After 6 days of infection, cells are recovered with lyse buffer and suspended. The solution cells is centrifiged 15 minutes at 16000 g at 4° C. The supernatant is sonicated then completed with lyse buffer. After 2 hours incubation at 4° C. under agitation, the solution is centrifuged at 4° C., 20 minutes at 16000 g. The supernatant obtened is store at −80° C.

Sphingosine Kinase Activity Assay

Sphingosine kinase activity was assayed using a 2 formats of scintillation proximity assay (SPA):

Sphingosine Kinase Activity Assay in 96 Wells Plate Format a) Assay Composition

The total volume of this assay is 100 µL comprising 2 µL of compound dissolved in DMSO or DMSO alone with 60 µL Assay Buffer containing triton micelles with [$^3$H]-Sphingosine and 38 µL Enzyme dilution in SK Buffer.

The Composition of the assay is the following: The Enzyme at the appropriate dilution is mixed with 0.125µCi/well [$^3$H]-Sphingosine, 1 µM Sphingosine, 30 µM ATP and 0.25% Triton, the compound to assayed at 12 different concentrations, 20 mM TRIS, 1 M β-mercaptoethanol, 1 mM EDTA, 0.5 mM 4 deoxypyridoxine, 40 mM β-glycerophosphate, 1 mM Orthovanadate, 10 mM $MgCl_2$ and 20% glycerol The enzyme is diluted in SK buffer. The dilution choosen is the one that leads to about 10% consumption of 1 µM Shingosine. This dilution is prepared at 0° C. and added to the assay at this temperature.

b) Assay Protocol

The assay is carried out in 96 well plates (Isoplate, Wallac with clear well in white matrix). Each plate includes 8 compounds at 11 singulates concentrations ($I_1$–$I_{11}$), 6 total activity wells (TA) and 2 non specific wells (NS) containing only DMSO.

The following solutions are first prepared:

SKx1 buffer: Tris 20 mM, MgCl2 10 mM, β-mercaptoethanol 1 mM, EDTA 1 mM, 4 Deoxypyridoxine 0.5 mM, β-glycerophosphate 40 mM, Sodium orthovanadate 1 mM, glycerol 20%,pH 7.4

SPA beads solution: SPA beads 5 mg/ml, Zncl2 40 mM, Glycerol 70%

Inhibitor dilutions with DMSO: For each inhibitor, 11 dilutions $I_1$–$I_{11}$ are prepared on a polypropylene mother plate.

Assay Buffer (for 1 plate): 5676 µl SK buffer containing protease inhibitor coktails with 19 µL Sphingosine (0.5 mM), 12 µl [3H]-Sphingosine (17 Ci/mmol, 1 mCi/ml), 29 µL ATP (10 mM) and 24 µl Triton 100X. The mixture is sonicated for few minutes to form micelles emulsion The different constituents are then distributed in the Isoplate:

DMSO (2 µL/well) is added in the TA wells and NS Wells.

Inhibitor dilutions are distributed in wells (2 µL/well)

Assay Buffer containing triton micelles with [$^3$H]-Sphingosine (60 µl/well)

Enzyme (38 µL/well) at the appropriate dilution is added in all the wells except NS wells The plate is stirred at 800 rpm and incubate for 45 min at room temperature 100 µL/well of SPA beads emulsion (corresponding to 0.5 mg/well beads). The plate is covered with a transparent Topseal (Packard), stirred for 1 hour at 800 rpm and counted on a Wallac Trilux.

This assay could be carried out at room temperature and the distribution of constituents could be altered if necessary.

Sphingosine Kinase Activity Assay in 384 Wells Plate Format a) Assay Composition The total volume is 30 µL comprising 3 µL of test compound dissolved in 25% DMSO or 25% DMSO alone with 14 µL assay buffer containing triton micelles with [$^3$H]-Sphingosine and 13 µL enzyme dilution in SK Buffer.

The composition of the assay is the following:

The enzyme at the appropriate dilution is mixed with 0.042 µCi/well [$^3$H]-Sphingosine, 1 µM Sphingosine, 30 µM ATP and 0.25% Triton, 20 µM of test compound, 20 mM TRIS, 1 mM β-mercaptoethanol, 1 mM EDTA, 0.5 mM 4 deoxypyridoxine, 40 mM β-glycerophosphate, 1 mM Orthovanadate, 10 mM MgCl$_2$ and 20% glycerol.

The enzyme is diluted in SK buffer. The dilution choosen is the one that leads to about 10% consumption of 1 M Shingosine and 30 µM ATP. This dilution is prepared at 0° C. and added to the assay at this temperature.

b) Assay Protocol

The assay is carried out in 384 well plates (white 384-well plate in white matrix). Each plate includes 23 or 32 compounds at 11 or 12 singulates concentrations (I1–I11 or 12), 8 total activity wells (TA) and 4 non specific wells (NS) containing only DMSO.

The following solutions are first prepared:

SKx1 buffer: Tris 20 mM, MgCl2 10 mM, β-mercaptoethanol 1 mM, EDTA 1 mM, 4 Deoxypyridoxine 0.5 mM, β-glycerophosphate 40 mM, Sodium orthovanadate 1 mM, glycerol 20%,pH 7.4

Leadseeker beads solution: SPA beads 17 mg/ml, Zncl2 40 mM, Glycerol 20%

Inhibitor dilutions with DMSO. For each inhibitor, 11 dilutions I$_1$–I$_{11}$ are prepared on a polypropylene mother plate.

Assay Buffer (for 1 plate): 5273 µl SK buffer containing protease inhibitor coktails with 23 µL Sphingosine (0.5 mM), 16 µl [3H]-Sphingosine (17 Ci/mmol, 1 mCi/ml), 35 µL ATP (10 mM), 29 µl Triton 100X The reaction mixture is sonicated for few minutes to form micelles emulsion The different constituents are then distributed, in the white matrix plate (possibly at room temperature):

25% DMSO (3 µL/well) is added in the TA wells and NS Wells.

Inhibitor dilutions in 25% DMSO are distributed (3 µL/well)

Assay Buffer containing triton micelles with [$^3$H]-Sphingosine (14µ/well)

Enzyme (13 µL/Well) at the appropriate dilution is added in all the wells except NS wells The plate is incubated for 45 min at room temperature 30 µL/well of leadseeker beads emulsion (corresponding to 0.5 mg/well beads)

The plate wait between 1 hour to 24 hours before is counted on a Leadseeker (Amersham Pharmacia biotech)

The distribution of constituents could be altered is necessary.

Assays Quantitation:

The quantitation of each assay needs that the raw data are transfered on a software (such as Excel 97) where percentages of inhibition are calculated using the following formula:

% Inhibition=100×(1−(Inhibited activity$_{cpm}$−NS$_{cpm}$)/(sTA$_{cpm}$−NS$_{cpm}$))

The % Inhibition are then fitted using the model <<Sigmoidal curve with Hill slope, y=100*X^n/(K^+X^n)<<.K is the desired IC50.

EXAMPLES

Example 1

Screening Assay Setting Up

Figure 1:
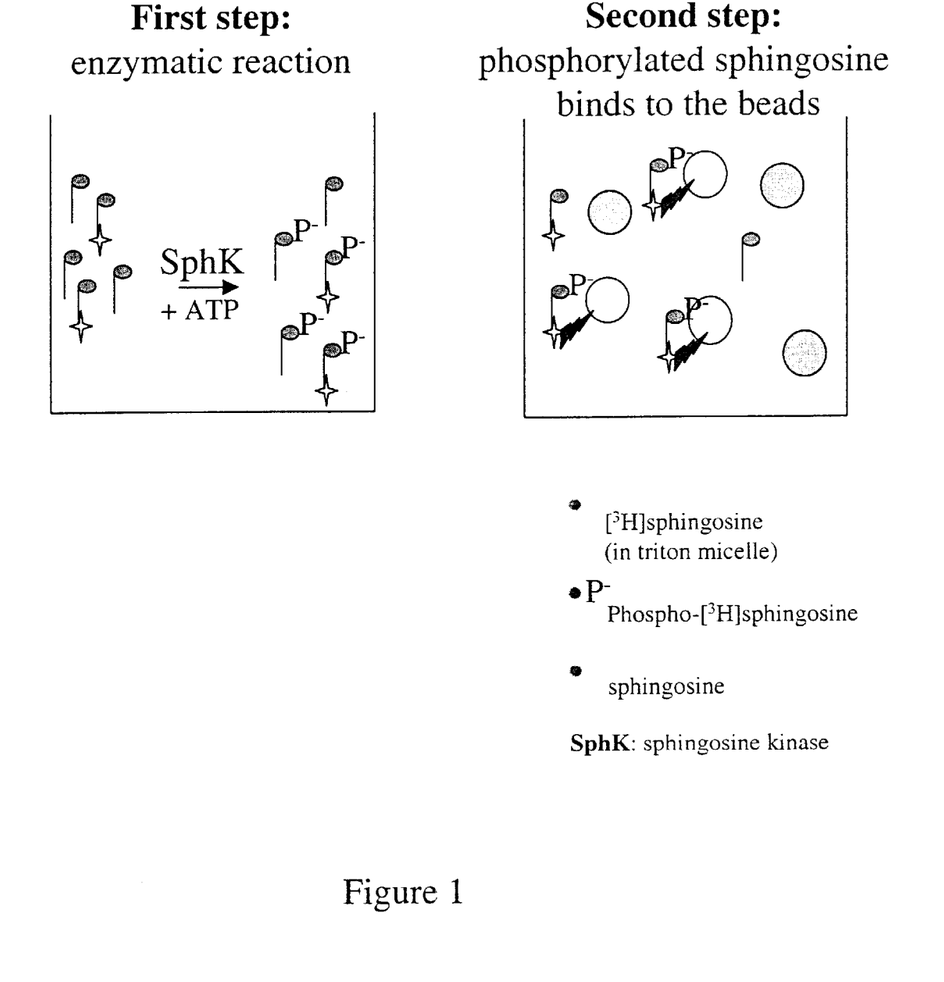
FIG. 1: Schematic representation of the SPA based assay

The sphingosine kinase (SPHK) activity is classically measured using $^{33}$P or $^{32}$P incorporation, followed by lipid extraction and thin layer chromatography separation of $^{33}$P or $^{32}$P sphingosine-1-P (A. Melendez et al., 2000). Although this test is very sensitive, it is not suitable for high throughput screening. It has now been discovered by the inventors that particular support material (such as "RNA binding SPA beads") have the ability to specifically bind phosphorylated lipids and not unphosphorylated lipids. Taking advantage of the property of these supports, a two-steps assay was set up (see FIG. 1). The first step, enzymatic phosphorylation of sphingosine, is based on the test described above. The enzyme is incubated for an hour with ATP and [$^3$H] sphingosine incorporated in triton micelles. In a second step, beads are added to the wells and the mix is agitated for 15 minutes, allowing the phosphorylated tritiated sphingosine to bind to the beads. According to the SPA principle, the β emission of the tritium bound to the beads (via the phosphorylated tritiated sphingosine) induce the beads to scintillate, whereas the tritium of unphosphorylated sphingosine, not closed enough, does not. The beads settle down for an hour, and the plate is read on a scintillation counter.

Example 2

Demonstration of Screening Assay Specificity

Figure 2:
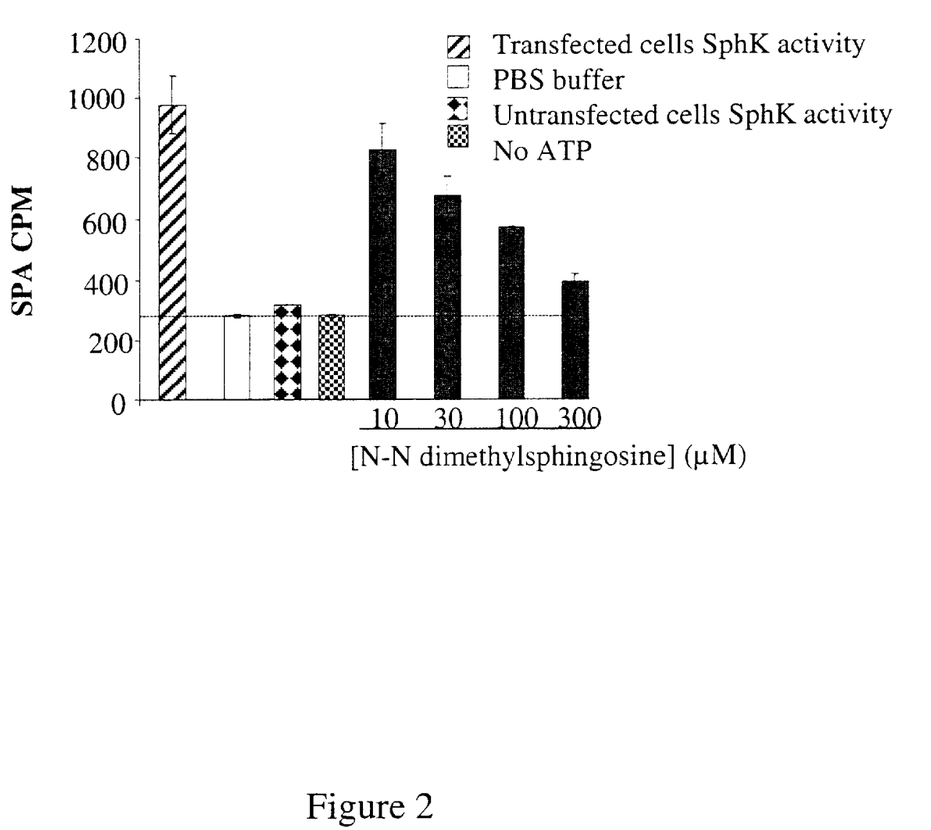
FIG. 2: Specificity of the kinase activity

The specificity of the test was assessed using untransfected cells such as CHO or COS7 cells which exhibited a low endogenous sphingosine kinase activity compared to transfected cells (FIG. 2), as previously described (A. Melendez et al., 2000). FIG. 2 shows that absence of ATP prevent activity, and that the already described SPHK inhibitor N-N-dimethylsphingosine blocked the enzyme activity with an IC50 in good agreement with previous results. These data strongly suggested that the activity detected in this assay correspond to the SPHK activity.

Example 3

Figure 3:
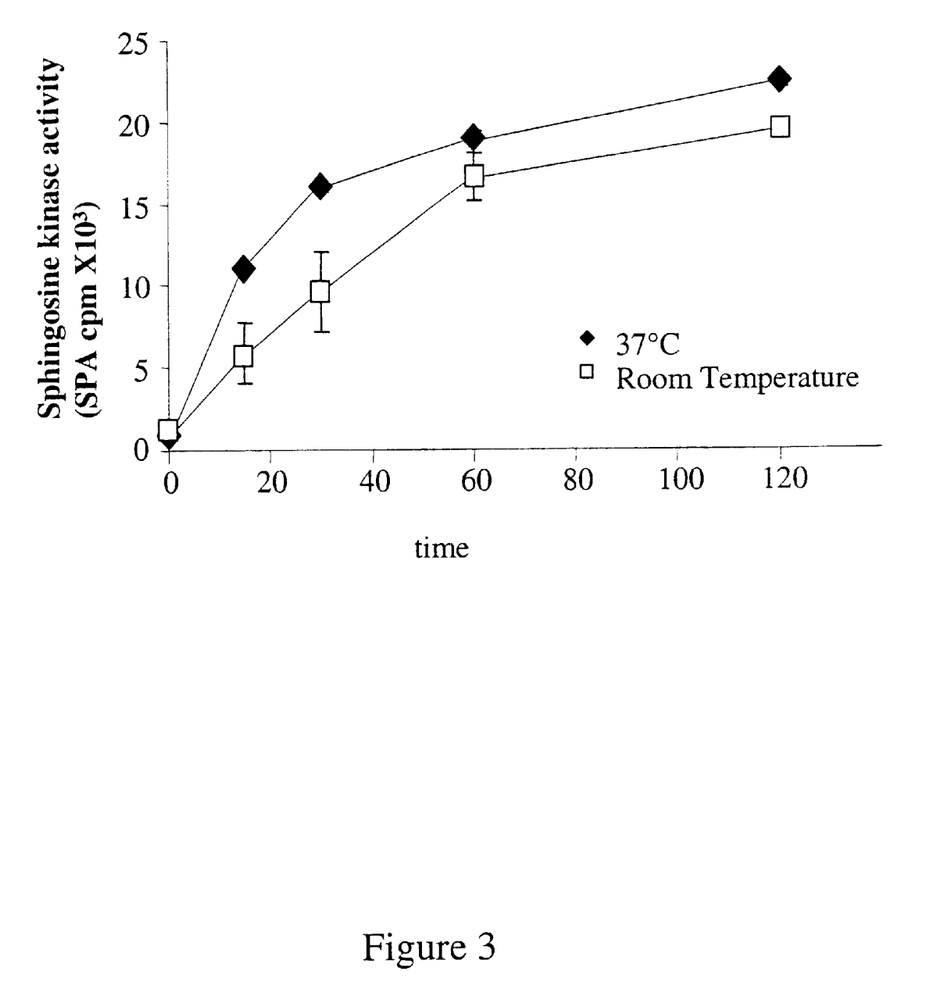
FIG. 3: Effect of incubation temperatures on SphK activity

Comparison of Efficiency of the Screening Assay at 37° C. and at Room Temperature The signal to noise ratio has been greatly increased using optimized conditions. The temperature at which the assay is performed is one of these conditions. In order to avoid a 37° C. incubation during the robotic process, room temperature and 37° C. activity of the enzyme was compared. As shown in FIG. 3, at one hour incubation time, activities at both incubation temperatures were found equivalent.

Example 4

Determination of ATP and Sphingosine Quantity

Figure 4:
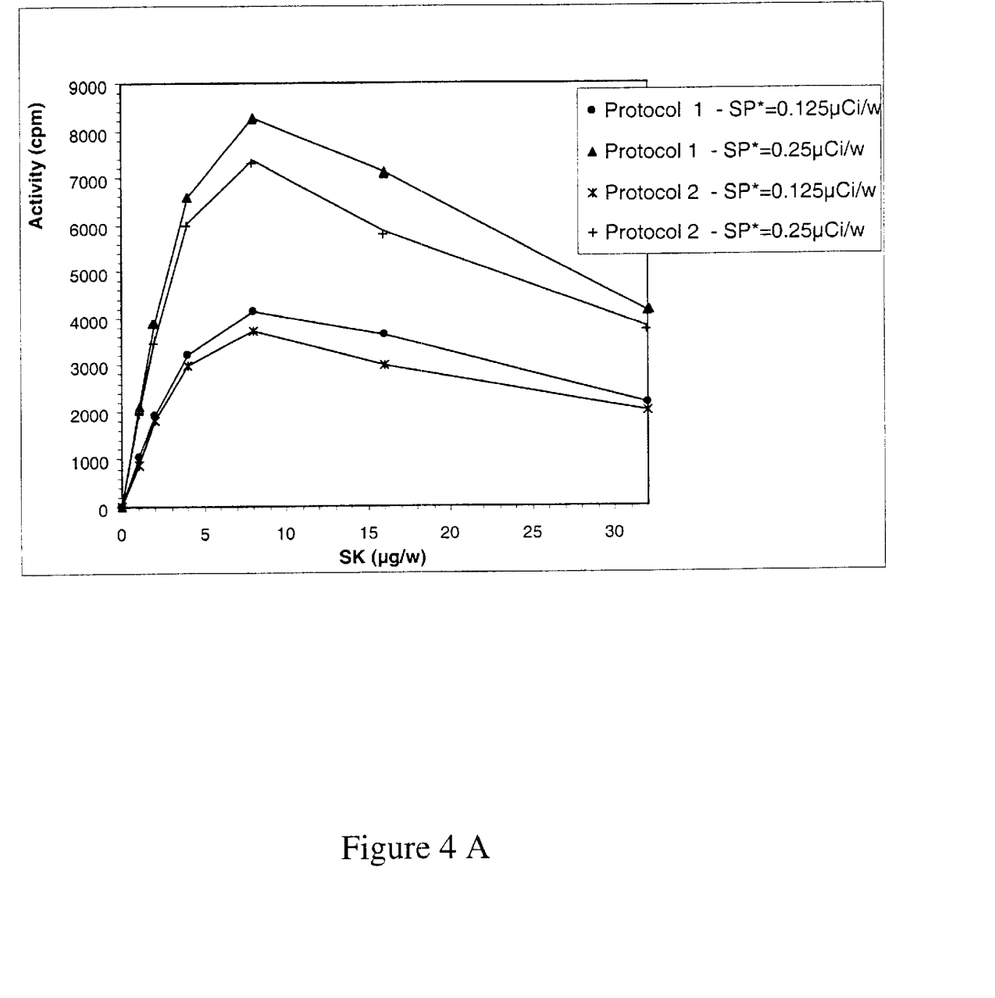

Optimization of assay conditions need also the determination of adequate quantities of ATP, sphingosine, and enzyme concentration. Since the ATP pocket of SPHKs does not exhibit a high homology with other kinases pocket (A. Melendez, personal communication), ATP binding pocket blockers might be specific inhibitors of these kinases. It might be then important to be able to sort them out. To detect sphingosine kinases inhibitors with a high sensitivity, substrate concentrations, i.e. sphingosine as well as ATP concentrations, should then preferably be below their respective K$_M$. Sphingosine K$_M$ is 5 µM (A. Melendez, et al., 2000) and the ATP $K_M$ is around 30 µM (FIG. 4B). The preferred concentration of ATP has been set up at 10 µM and the concentration of sphingosine at 1 µM. Furthermore, FIG. 4A indicated that the maximal enzyme activity (Vmax) is reached with 2 µg of cell extract. The amount of enzyme is therefore set up at 1 µg of cell extract per well.

Example 5

Comparison of Triton Quantity

Figure 5:
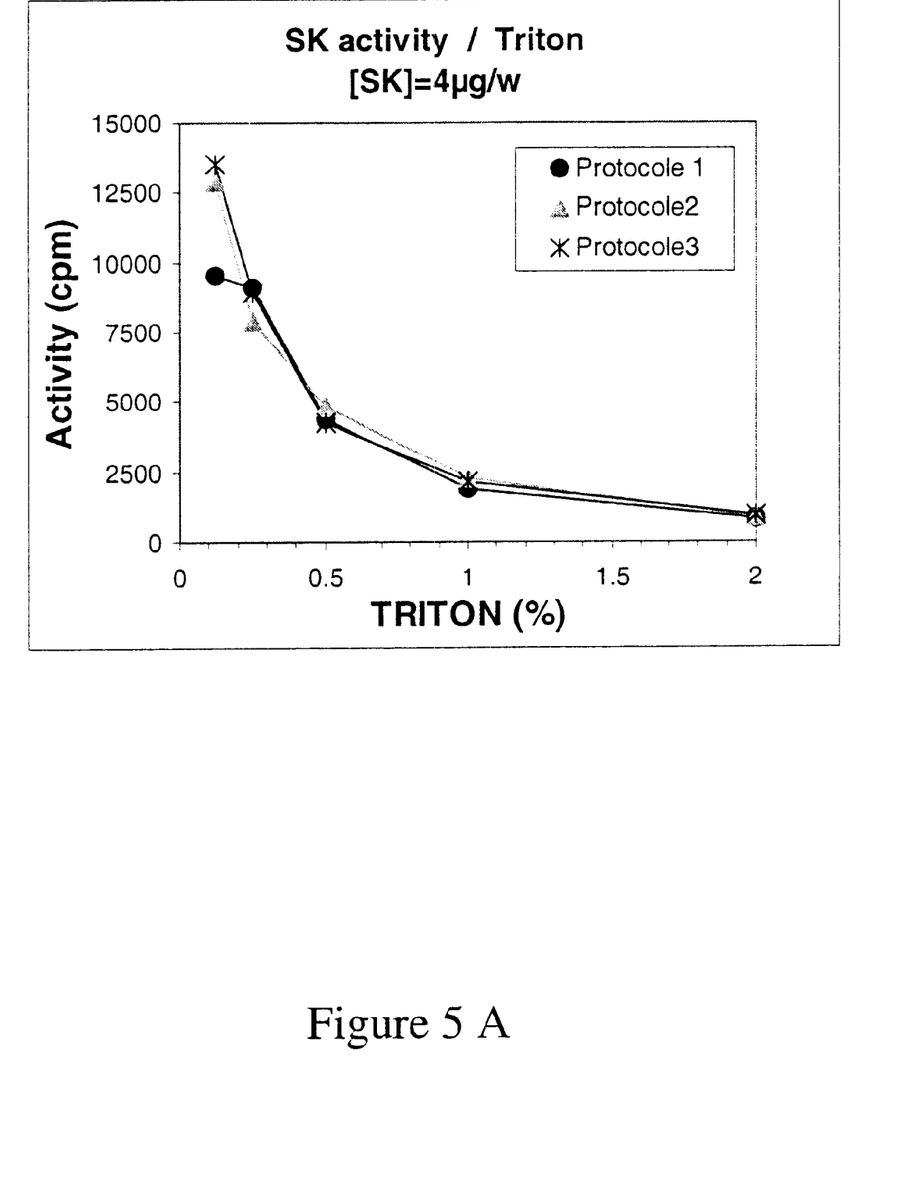
Figure 6:
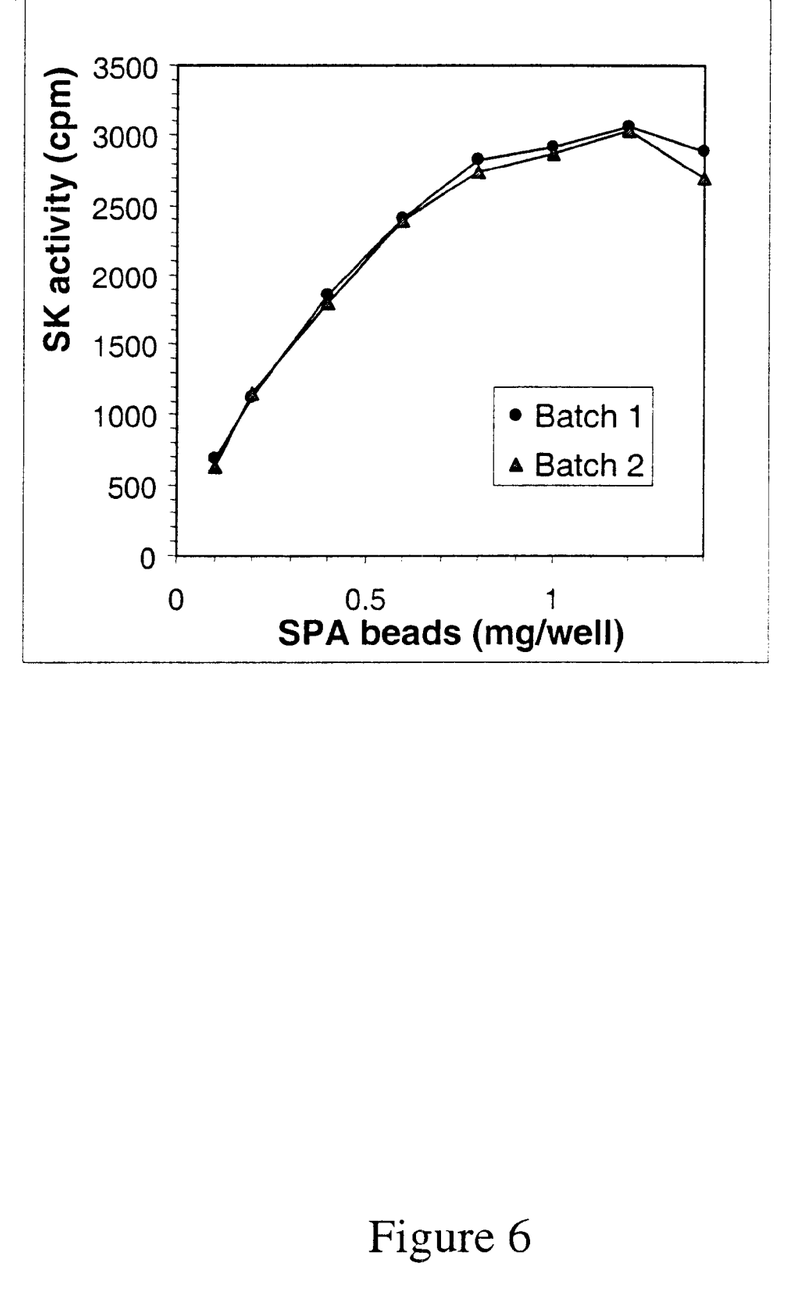
FIG. 6: SPA beads quantity optimisation

To improve the signal, quality of the triton micelles in which sphingosine was incorporated was also checked. FIG. 5A compares the sphingosine kinase activity according to several quantities of Triton X-100 (%). This example shows that maximum of sphingosine kinase activity is between 0.25% and 1.0% triton with an optimal activity at 1% triton.

Example 6

Comparison of Sphingosine Activity With Different Concentrations of DMSO

Compounds from main libraries are dissolved in DMSO. It is therefore important to validate the assay in presence of various amount of this solvent. FIG. 5B compares the sphingosine kinase activity according to several quantities of DMSO (%). Accordingly, this example shows that, although DMSO decrease the signal by 20%, up to 10% DMSO did not block the SphK activity, indicating that the solvent will not diminish the quality of the test.

Example 7

Sphingosine Kinase Activity in Lymphocytes (Jurkat Cells)

Figure 7:
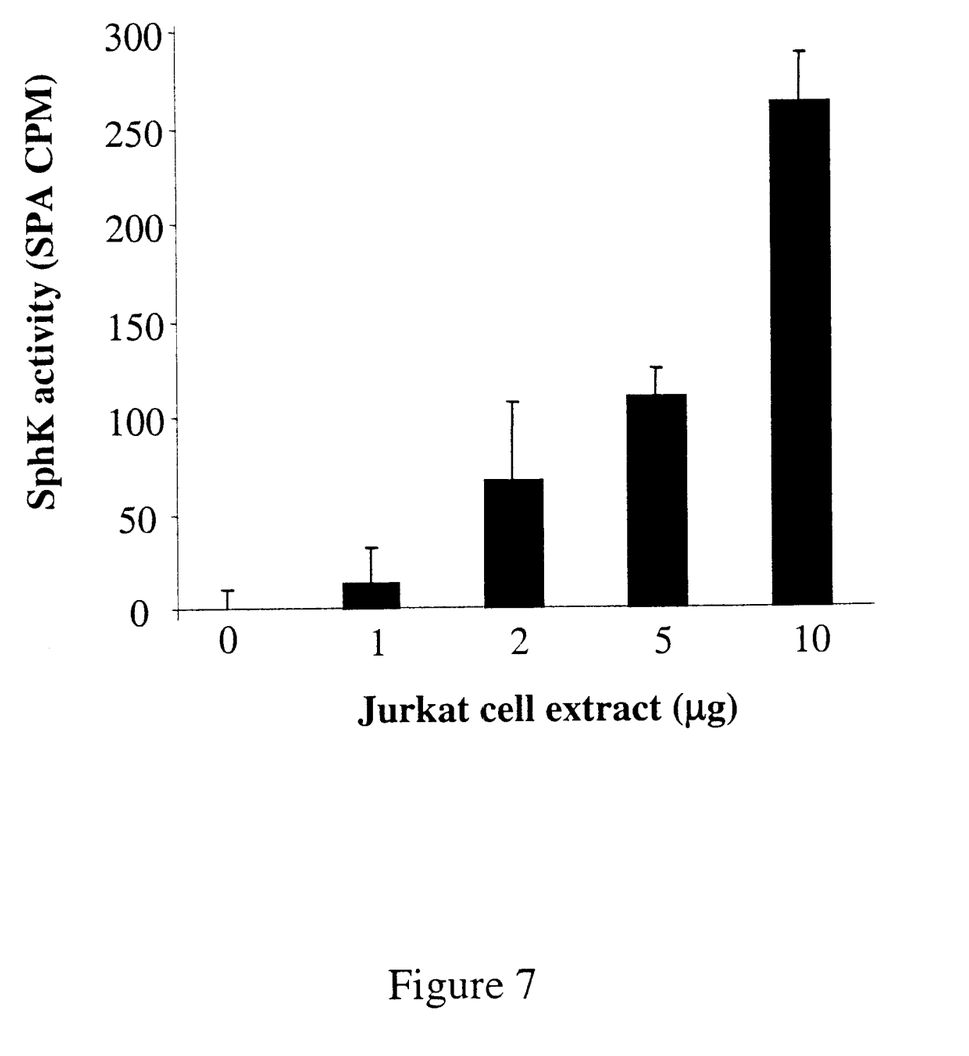
FIG. 7: SphK activity in Jurkat cells (lymphocytes)

This example shows the expression of sphingosine kinase activity in other cell type as CHO or COS-7 and more particularly in lymphocytes. According to FIG. 7 sphingosine kinase activity is recorded according to several quantities of proteine (enzyme) in Jurkat cells extracts.

In conclusion, according to the preceeding examples a sphingosine kinase SPA test has been set up, using tritiated sphingosine and RNA binding beads. This test is very robust, both on 96 and 384 wells format, and allows us to screen quickly compounds libraries to sort out inhibitors of both ATP and sphingosine binding pockets with an exquisite sensitivity due to the low concentrations of both ATP and sphingosine which are used. This test doesn't require purified enzyme, but instead, is run using raw extracts of transiently transfected cells. This is the first non $_{33}P$ or $^{32}P$-containing assay described so far for sphingosine kinase. Other lipid kinases might be screened using this technique.

We claim:

1. A method of selecting or identifying a compound that modulates, inhibits or activates the activity of a lipid kinase, comprising (i) mixing the lipid kinase and a labeled lipid substrate thereof in the presence of a candidate compound and a source of phosphate to form a reaction mixture, (ii) exposing the reaction mixture of (i) to a support material, wherein the support material binds lipid substrate in a phosphorylated form and essentially does not bind an unphosphorylated lipid, and (iii) assessing the amount of phosphorylated lipid bound to the support, said amount being an indication of the activity of said lipid kinase, allowing the selection or identification of a compound that modulates, inhibits or activates said activity.

2. The method of claim 1, wherein the support material comprises components selected from yttrium-silicate, yttrium-oxide or polyvinyltoluene (PVT).

3. The method of claim 1, wherein the support material comprises (poly)acrylamide, agarose, sepharose or polystyrene 4.

4. The method of claim 1, wherein the support material is a bead or a Scintillation Proximity Assay (SPA) bead.

5. The method of claim 1, wherein the support material contains a scintillant.

6. The method of claim 1, wherein the lipid substrate is radio-labelled.

7. The method of claim 1, wherein the lipid substrate is in a micelle.

8. The method of claim 1, wherein the lipid kinase is a cell or membrane extract.

9. The method of claim 1, wherein the lipid kinase is a recombinant enzyme.

10. The method of claim 1, wherein the source of phosphate is ATP.

11. The method of claim 1, wherein the reaction mixture in (i) comprises:
   0.01 to 10 µM of unlabeled lipid
   0.01 to 10 µCi of radio-labelled lipid,
   0.1 to 5% of detergent, neutral lipid or serum proteins from mammalian origin; or a mixture thereof,
   0.1 µM to 1 mM of phosphate source, and
   a lipid kinase.

12. The method of claim 11, wherein 0 to 30% of glycerol is further added to the reaction mixture.

13. Method according to claim 12, wherein 15% to 25% of glycerol is added to the reaction mixture.

14. Method according to claim 12, wherein 20% of glycerol is added to the reaction mixture.

15. The method of claim 11, wherein the neutral lipid is phosphatidyl serine or cardiolipine.

16. The method of claim 11, wherein the serum protein is Bovine Serum Albumin (BSA), Human Serum Albumin (HAS) or Foetal Bovine Serum Albumin (FBSA).

17. The method of claim 1, wherein the reaction mixture in (i) comprises:
   0.01 to 1 µM of unlabeled lipid
   0.01 to 0.5 µCi of radio-labelled lipid,
   0.1 to 1% of detergent,
   0.1 µM to 50 µM of phosphate source, and
   0.1 to 40 µg of total proteins of a cell preparation comprising a lipid kinase.

18. The method of claim 1, comprising comparing the amount of lipid bound to the support material in the presence and in the absence of a candidate compound, and identifying the compound that modulates said amount.

19. The method of claim 1, wherein several candidate compounds are tested in parallel.

20. The method of claim 1, wherein step (i) is performed in a microtitration plate.

21. The method of claim 1, wherein the lipid kinase is a membrane, cytosolic or secreted lipid kinase.

22. The method of claim 1, wherein the lipid kinase is a sphingosine kinase.

23. The method of claim 1, wherein the lipid substrate is sphingosine.

24. A method of selecting or identifying a compound that modulates, inhibits or activates, the activity of a sphingosine kinase, comprising (i) mixing the said sphingosine kinase and a radio-labelled sphingosine in the presence of a candidate compound and a source of phosphate, (ii) exposing the reaction mixture of (i) to a support material, wherein the support material binds phosphorylated sphingosine and essentially does not bind unphosphorylated sphingosine, and (iii) assessing the amount of sphingosine-1-P bound to the support, said amount being an indication of the activity of said sphingosine kinase, allowing the selection or identification of a compound that modulates, inhibits or activates said activity.

25. The method of claim 24, wherein the support material is an yttrium-silicate SPA bead.

26. The method of claim 24, wherein the support material is an yttrium-oxide SPA bead.

* * * * *